United States Patent
Pozzoli et al.

(10) Patent No.: US 9,663,450 B2
(45) Date of Patent: May 30, 2017

(54) PROCESS FOR THE PURIFICATION OF MELPHALAN

(71) Applicant: FARMABIOS S.P.A., Gropello Cairoli (PV) (IT)

(72) Inventors: Claudio Gianluca Pozzoli, Gropello Cairoli (IT); Valentina Canevari, Gropello Cairoli (IT); Matteo Curti, Gropello Cairoli (IT)

(73) Assignee: FARMABIOS S.P.A., Gropello Cairoli (PV) (IT)

( * ) Notice: Subject to any disclaimer, the term of this patent is extended or adjusted under 35 U.S.C. 154(b) by 0 days.

(21) Appl. No.: 14/890,540

(22) PCT Filed: May 27, 2014

(86) PCT No.: PCT/EP2014/060987
§ 371 (c)(1),
(2) Date: Nov. 11, 2015

(87) PCT Pub. No.: WO2014/191426
PCT Pub. Date: Dec. 4, 2014

(65) Prior Publication Data
US 2016/0090352 A1     Mar. 31, 2016

(30) Foreign Application Priority Data
May 31, 2013  (IT) .............. MI2013A0896

(51) Int. Cl.
| C07C 229/00 | (2006.01) |
| C07C 227/40 | (2006.01) |
| C07C 227/20 | (2006.01) |
| C07C 269/06 | (2006.01) |
| C07C 269/08 | (2006.01) |
| C07C 229/36 | (2006.01) |

(52) U.S. Cl.
CPC .......... *C07C 227/40* (2013.01); *C07C 227/20* (2013.01); *C07C 229/36* (2013.01); *C07C 269/06* (2013.01); *C07C 269/08* (2013.01)

(58) Field of Classification Search
None
See application file for complete search history.

(56) References Cited

U.S. PATENT DOCUMENTS

| 3,032,584 A | 5/1962 | Bergel et al. |
| 3,032,585 A | 5/1962 | Bergel et al. |
| 2009/0240074 A1 | 9/2009 | Jobdevairakkam et al. |
| 2010/0311838 A1* | 12/2010 | Pipkin .................. A61K 9/0019 514/564 |
| 2012/0116117 A1 | 5/2012 | Gurjar et al. |
| 2012/0190887 A1 | 7/2012 | Zhou |

FOREIGN PATENT DOCUMENTS

| CN | 101100400 | 1/2008 |
| EP | 0317281 | 5/1989 |
| GB | 750155 | 3/1954 |
| GB | 783292 | 9/1957 |
| WO | 2009117164 | 9/2009 |

OTHER PUBLICATIONS

Pu et al. Molecular Pharmacology (1999), vol. 56, pp. 147-153.*
International Search Report based on International Application No. PCT/EP2014/060987.

* cited by examiner

*Primary Examiner* — Patrick Lewis
(74) *Attorney, Agent, or Firm* — Lucas & Mercanti, LLP

(57) ABSTRACT

A method for the purification and preparation of melphalan that allows to obtain melphalan with purity higher than 99.5% is described.

12 Claims, No Drawings

PROCESS FOR THE PURIFICATION OF MELPHALAN

CROSS-REFERENCE TO RELATED APPLICATIONS

This application is a 371 of PCT/EP2014/060987 filed May. 27, 2014, which claims the benefit of Italian Patent Application MI2013A000896, filed May 31, 2013.

FIELD Of THE INVENTION

The present invention relates to a method for the purification of melphalan.

BACKGROUND OF THE INVENTION

Melphalan is the L enantiomer of 4-[bis(2-chloroethyl)amino]phenylalanine of formula I:

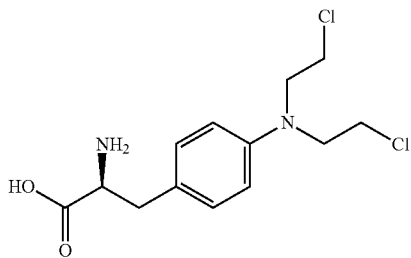

This compound is also known with the name of L-PAM, L-sarcolysine, NCS-8806, CB3025.

Melphalan is commercially known with the name of Alkeran™ in the form of tablets or injectable preparations.

Melphalan is a compound known for its antitumor properties; its D enantiomer and the racemic mixture also have antitumor activity but of small degree.

Melphalan is particularly used in the treatment of multiple myeloma and ovarian cancer.

Melphalan is synthesized according to the processes disclosed in U.S. Pat. Nos. 3,032,584 and 3,032,585 starting from DL-phenylalanine with a process comprising the following steps:
1. nitration in the presence of nitric acid and sulfuric acid;
2. protection of the glycine amino group as acetyl, formyl or phthaloyl derivative followed by esterification of the carboxy group;
3. reduction of the nitro group to amine by hydrogenation;
4. hydroxyethylation reaction of the amine on the aromatic ring in the presence of ethylene oxide;
5. chlorination in the presence of $POCl_3$ or $SOCl_2$;
6. resolution of the racemic mixture and isolation of L-enantiomer;
7. deprotection of the glycine amino group and hydrolysis of the ester.

RO 57195 discloses the isolation of melphalan hydrochloride by adding diethyl ether to the aqueous solution containing it, followed by the addition of $Na_2CO_3$ or NaOAc to bring the pH to 0.5 and subsequently to 1.5-2. The purification is carried out by dissolving in HCl melphalan hydrochloride obtained by the treatment at pH=2.

GB 750,155 discloses the synthesis of melphalan starting from 4-[bis(hydroxyethyl)amino]phenylalanine ethyl ester by reaction with $POCl_3$ or $SOCl_2$ in the optional presence of an inert solvent to give the chlorine derivative followed by a reaction with HCl to remove the protective groups.

GB 783,292 discloses the synthesis of melphalan starting from its non optically active precursors by resolution of some intermediates of the synthesis as brucine salts. It is particularly disclosed the separation of brucine diastereomeric salts of N-acetyl-4-nitro-DL-phenylalanine. The L-isomer, suitably purified from the residues of brucine, is hydrolysed to give 4-nitro-phenylalanine, followed by the esterification with phthalic anhydride, the reduction of the nitro group, the reaction of the resultant amine with ethylene oxide, the reaction with $POCl_3$ or $SOCl_2$ to obtain the chlorine derivative, the removal of the phthaloyl protective group and of the ethyl ester to give 4-bis-(2-chloroethyl)-aminophenylalanine.

CN 101100440 discloses a process for the preparation of melphalan hydrochloride comprising:
  the esterification of the carboxyl group of 4-nitrophenylalanine in EtOH
  the protection of the amine in the presence of TEA to give the N-Boc derivative
  the hydrogenation of the nitro group
  the hydroxyethylation reaction in the presence of ethylene oxide
  the chlorination reaction of the OH groups
  the deprotection reaction of the amino group
  the hydrolysis reaction with 2M-6M hydrochloric acid to remove the protective groups and to obtain the final compound.

EP 0 317 281 discloses the preparation of melphalan hydrochloride by reaction of the N-phthaloyl derivative with ethylene oxide, followed by chlorination, hydrolysis and subsequent formation of melphalan hydrochloride.

WO 2009/117164 discloses a process for the synthesis of melphalan characterized by the fact that the hydroxyethylation reaction of the aromatic $NH_2$ group is carried out without the need to protect the glycine $NH_2$ group.

US 2012/0190887 discloses a process for the preparation of pharmaceutical grade melphalan hydrochloride comprising a purification step by dissolving in hydrochloric acid, adding active charcoal, adding alkali hydroxide, filtering and washing with deionized water, slurrying with isopropyl ether.

US 2012/0116117 discloses a process for the preparation of melphalan hydrochloride with HPLC purity >99% i.e. conforming to drug regulation specifications.

In the processes described in the state of the art, melphalan is isolated and purified through some steps that provide a precipitation of melphalan in water saturated with sodium acetate at pH=7 followed by one or more crystallizations from methanol or a precipitation in the presence of diethylamine at pH=7, followed by washing with methanol.

Most of the purification methods disclosed in the state of the art need to bring the pH to neutrality after the treatment with aqueous hydrochloric acid necessary for the removal of the amine and carboxy protective groups, to allow the precipitation of melphalan.

These purification methods yield melphalan with a purity from 96% to 99%.

The precipitation of melphalan at pH=7, according to the processes known in the state of the art, leads to the formation of a highly unstable solid which is particularly hard to filter because of its sponginess. The instability of said spongy solid leads to the formation of an impurity, called "dimer" (impurity G—4-[[2-[[4-[bis(2-chloroethyl) amino]-L-phenylalanine]oxy]ethyl]-(2-chloroethyl)amino]-L-phenylalanine) according to European Pharmacopeia 2012, pages 4658-4659). The limit values of such impurity, reported into the European Pharmacopeia, are high (limit NMT 1.0%) just because of the difficult in the removal of the "dimer" in the process for the production of melphalan.

SUMMARY OF THE INVENTION

We have now found a method for the purification of melphalan that allows to obtain melphalan with much higher purity than that required by the European Pharmacopeia, particularly with a purity higher than 99.5%, preferably higher than 99.8%, in which each single impurity identified by the European Pharmacopeia is NMT 0.5%, preferably NMT 0.2%. Particularly, the impurity G is preferably NMT 0.2%, most preferably NMT 0.1%.

Melphalan obtained after the treatment at pH=2 in the presence of water, methyl-tert-butyl ether and diethylamine is characterized by the absence of ionizable chlorides by HPLC analysis and will be herein after indicated as "melphalan base".

DETAILED DESCRIPTION OF THE INVENTION

It is therefore an object of the present invention a process for the purification of melphalan comprising:
(a) the treatment of a compound of formula IV

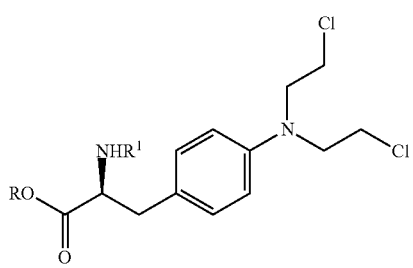

IV wherein R is hydrogen or a linear or branched $C_1$-$C_6$ alkyl group, preferably selected among ethyl, methyl, propyl, most preferably ethyl and $R^1$ is hydrogen or an amine protective group, preferably selected among phthaloyl or tert-butoxycarbonyl, more preferably tert-butoxycarbonyl; or a hydrochloric salt or a dimeric form thereof, in HCl 37% under reflux;
(b) the isolation of the compound obtained from step (a) in the presence of water, methyl-tert-butyl ether and diethylamine at pH=2.

The process for the purification object of the present invention is followed by washing the compound obtained from step (b) with a linear or branched $C_1$-$C_4$ alcohol, preferably selected among methanol, ethanol and isopropanol, more preferably ethanol. Said washing allows to remove the diethylammonium salts obtained from treatment (b). The product obtained by said washing can be stored as such at low temperatures to avoid the formation of dimerization products or can be salified with gaseous HCl which is added as an ethanol solution in acetone to give melphalan hydrochloride.

The process for the purification object of the present invention allows to obtain melphalan with a HPLC purity greater than 99.5%, preferably greater than 99.8%.

The step (a) of the process object of the present invention is preferably carried out under reflux for at least 16 hours. The ratio HCl 37%/melphalan (titrated) is preferably of about 4:1.

The step (b) is preferably taken at a temperature from 0° C. to 10° C.

The ratio water/melphalan (titrated) is preferably of about 10:1, the ratio methyl-tert-butyl ether/water is of about 2:1. In step (b) of the process object of the present invention melphalan with a HPLC purity greater than 99.5%, preferably greater than 99.8%, is obtained.

The method for the purification object of the present invention comprises the treatment of melphalan or one of its derivative of formula IV optionally in a protective and/or salified form, or as a "dimer", both as a product or an isolated intermediate of the synthesis, both as a reaction crude, in the presence of HCl 37% under reflux, followed by the treatment at pH=2 of the resultant compound.

The treatment with HCl37% under reflux allows to obtain melphalan dissolved in solution with a purity greater than 99.5%, preferably greater than 99.8%. Said treatment allows to hydrolyze any protective groups on the molecule and to purify, at the same time, the resultant product by hydrolysis of any impurities in the reaction medium such for example esters, dimers, trimers of melphalan.

The isolation of the product after the treatment with HCl 37% under reflux is carried out by treatment at pH=2 in the presence of diethylamine and methyl-tert-butyl ether. The isolated product is characterized by the absence of ionizable chlorides and by a low ability to form undesirable by-products, such as for example the "dimer" (impurity G).

The process for the purification object of the present invention can be used to obtain melphalan with a high purity (greater than 99.5%) both starting from a reaction crude and from melphalan with a low purity degree or from a derivative of formula IV thereof.

In a preferred embodiment the process for the purification object of the present invention is carried out at the end of a process of synthesis of melphalan which comprises:

1. the alkylation reaction of a compound of formula II

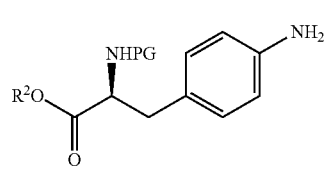

II wherein $R^2$ is a linear or branched $C_1$-$C_6$ alkyl group, preferably selected among ethyl, methyl, propyl, most preferably ethyl and PG is an amine protective group, preferably selected among phthaloyl or tert-butoxycarbonyl group, most preferably tert-butoxycarbonyl;
in the presence of an aprotic polar solvent, a base and an alkylating agent, preferably selected among iodoethanol, chloroethanol or ethylene oxide to give a compound of formula III

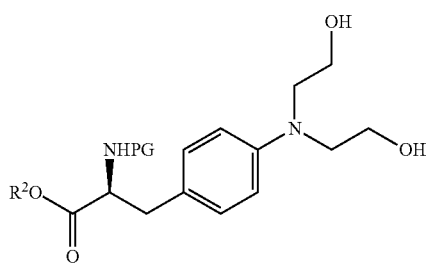

wherein R² and PG have the above reported meanings;
2. the chlorination reaction of the resultant compound of formula III in the presence of a chlorinating agent preferably selected among POCl₃ and SOCl₂ in a suitable solvent preferably selected among isopropylacetate or ethylacetate, preferably isopropylacetate to give a compound of formula IV-1

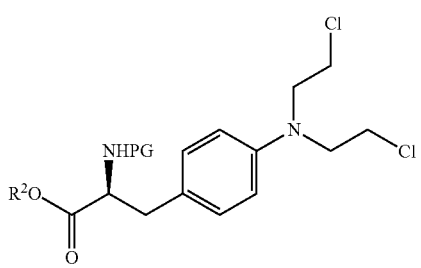

wherein R² and PG have the above reported meanings.

It is therefore a further object of the present invention a process for the preparation of melphalan comprising:
1. the alkylation reaction of a compound of formula II

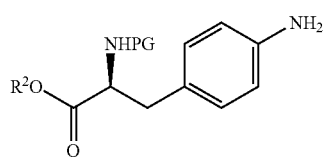

wherein R² is a linear or branched $C_1$-$C_6$ alkyl group, preferably selected among ethyl, methyl, propyl, most preferably ethyl and PG is an amine protective group, preferably selected among phthaloyl or tert-butoxycarbonyl group, most preferably tert-butoxycarbonyl;
in the presence of an aprotic polar solvent, a base and an alkylating agent, preferably selected among iodoethanol and chloroethanol or ethylene oxide to give a compound of formula III

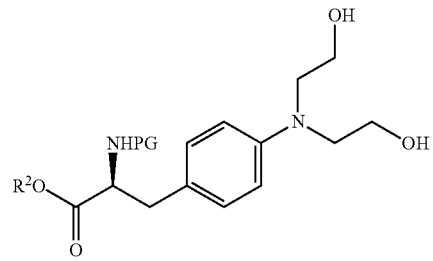

wherein R² and PG have the above reported meanings;
2. the chlorination reaction of the resultant compound of formula III in the presence of a chlorinating agent preferably selected among POCl₃ and SOCl₂ in a suitable solvent preferably selected among isopropylacetate or ethylacetate, preferably isopropylacetate to give a compound of formula IV-1

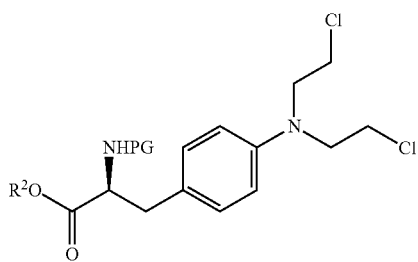

wherein R² and PG have the above reported meanings;
3. the isolation and purification of melphalan comprising:
   (a) the treatment of a compound of formula IV-1 in HCl 37% under reflux;
   (b) the isolation of the compound obtained from step (a) in the presence of water, methyl-tert-butyl ether and dietylamine at pH=2;
   (c) the washing of the compound obtained from step (b) with a linear or branched $C_1$-$C_4$ alcohol, preferably selected among methanol, ethanol, isopropanol, most preferably ethanol;
4. the optional treatment of the compound obtained from step (c) with a mineral acid, preferably with an ethanol solution of gaseous HCl in acetone.

In step 1) of the process object of the present invention the aprotic polar solvent is preferably selected among acetonitrile and dichloromethane, acetonitrile is preferably used; the base is preferably selected among $Na_2CO_3$, $K_2CO_3$, $Cs_2CO_3$, CaO, $Na_2CO_3$ is most preferably used.

In step 2) of the process object of the present invention POCl₃ in isopropylacetate is preferably used.

Preferably in step 4) of the process object of the present invention an ethanol solution of gaseous HCl in acetone is used in a concentration of from about 16% to about 25%.

A further preferred embodiment of the process object of the present invention consists of the synthesis and purification of melphalan comprising:
1) the alkylation reaction of the amine group on the aromatic ring of N-BOC-L-phenylalanine ethyl ester in the presence of acetonitrile, $Na_2CO_3$ and iodoethanol to give 4-(bis(2-hydroxyethyl)-amino-N-BOC-L-phenylalanine ethyl ester;

2) the chlorination reaction of the compound obtained in step 1) in the presence of POCl₃ and isopropylacetate;
3) the isolation and purification of melphalan comprising:
   (a) the treatment of the compound obtained in step 2) in the presence of HCl 37% under reflux;
   (b) the isolation of the compound obtained in step a) with water, methyl-tert-butyl ether and diethylamine at pH=2;
   (c) the washing of the compound obtained in step b) with ethanol;
4) the treatment of the compound obtained in step c) with an ethanol solution of HCl in acetone Melphalan and its hydrochloride salt having HPLC purity >99.5%, preferably >99.8% are a further object of the present invention.

The process object of the present invention allows to obtain melphalan with a HPLC purity greater than the processes known in the state of art. Particularly, the hydrolysis reaction reported in step a) allows to obtain high purities through the removal of further impurities in the mixture such as for example dimers, trimers, esters etc.

The purity result is surprisingly obtained only by using HCl 37% under reflux. In fact, using HCl at different concentrations, for example at 32%, melphalan with purity greater than 99.5% is not obtained while operating under the same conditions of the purification process according to the invention.

The subsequent isolation at pH=2 in step (b) surprisingly allows to obtain a compound with a high purity and characterized by a high stability in comparison to the spongy solid isolated under the neutral conditions described in the known art. The greater stability is probably given by a less capability to form the "dimer" (impurity G) compared to melphalan obtained according to the methods known in the state of art.

The washing of the compound reported in step (c) with ethanol allows to remove diethylammonium chloride salts, residues of step (b).

All the terms used in the present application, unless otherwise indicated, are to be understood in their common meaning as known in the art. Other more specific definitions for certain terms, as indicated in this application, are underlined later and are constantly applied for the whole description and the claims unless a different definition provides specifically a wider meaning.

The term "polar solvent" relates to a solvent which behave as a proton donor, such as water; an alcohol, for example, methanol, ethanol, propanol, iso-propanol, butanol, tert-butanol; or a polarized solvent, such as esters, for example ethyl acetate, butyl acetate, nitriles, for example acetonitrile; ethers, for example, tetrahydrofuran, dioxane; ketones, for example, acetone, methyl butyl ketone; and the like.

Further information about solvent can be found in organic chemistry books or in specialized monographs, for example *Organic Solvents Physical Properties and Methods of Purification,* 4th ed., John A. Riddik, et al., Vol II, in "Techniques of Chemistry Series", John Wiley & Sons, NY, 1986. Such solvents are known to the person skilled in the art and it is clear to the person skilled in the art that different solvents and mixtures thereof can be preferred, depending on the specific compounds and on the reaction conditions, being their choice influenced, for example, by solubility and reagent reactivity, by preferred temperature ranges.

Although the invention has been described in its characterizing features, the equivalents and modifications obvious to the skilled in the art are included in the following invention.

The present invention will now be illustrated by some examples which have not to be seen as limiting the scope of the invention.

EXAMPLE 1

Preparation of 4-(bis-(2-hydroxyethyl)-amino-N-BOC-L-phenylalanine ethyl ester

Into a suitable reactor A, 2.0 kg of N-BOC-L-phenylalanine ethyl ester and acetonitrile were loaded. The suspension was let under stirring until complete dissolution, maintaining the temperature at 23° C. and 1.5 kg of sodium carbonate were then added. Subsequently, 3.2 L of 2-iodoethanol were added dropwise, the solution was heated up to 85° C. and these conditions were maintained for 2 hours. At the end of the reaction the mixture was quickly cooled down to 20° C.

In another suitable reactor B, 35L of water and 4 kg of Celite® were loaded and the mixture was left under stirring for at least 5 minutes. The compound obtained into reactor A was transferred into reactor B and the suspension was kept under stirring for an hour. The suspension was filtered and washed with 12 L of water.

The wet Celite® obtained into the reactor B and 140 L of ethyl acetate were loaded into a reactor C and the mixture was kept under stirring for 30 minutes then filtered by collecting the filtrate into a reactor D and letting the phases separate. The organic phase was distilled at reduced pressure. The residue was purified by chromatography using methylene chloride/ethyl acetate about 2:1.

About 1.8 kg of 4-(bis-(2-hydroxyethyl)-amino-N-BOC-L-phenilalanine ethyl ester were then obtained.

EXAMPLE 2

Preparation of Melphalan hydrochloride 4-(bis-(2-hydroxyethyl)-amino-N-BOC-L-phenilalanine ethyl ester contained into the rich fractions was dissolved in 16 L of isopropyl acetate and dropped into 4.6 L of phosphoryl chloride, maintaining the temperature at 40° C., in an inert atmosphere. The solution was heated at 50° C. and the solution was kept under stirring for 2 hours and 30 minutes in an inert atmosphere.

At the end of the reaction the solution was then transferred into a separated funnel letting the phases separate for 30 minutes.

The phase containing the chlorinated product was dropped into 8.8 L of 37% HCl and let under stirring at 130° C. under reflux for at least 12 hours. The solution was subsequently cooled down to 50° C.

At the end of the reaction the solution was cooled down to 20° C. under stirring and subsequently concentrated at a reduced pressure.

To the concentrated residue were added 9 L of water, 18 L of methyl-tert-butyl ether and 2.6 L of diethylamine. The mixture was kept under stirring up to stable pH=2 and these conditions were maintained for 10 minutes, the mixture was subsequently filtered and washed with 10 L of methyl-t-butyl ether.

The resultant product was transferred into a suitable reactor and 18 L of ethanol at 99.9% were subsequently loaded. The suspension was left under stirring for at least 10 minutes, then filtered. The product was dried under vacuum for 8-12 hours obtaining melphalan.

Into a suitable reactor were loaded 0.7 Kg of melphalan, obtained as previously described, and 22 L of acetone, the solution was cooled down and kept under stirring for 30 minutes. The stoichiometric amount of gaseous HCl absorbed in ethanol was subsequently added according to the titration. The suspension was kept under stirring under cooling for a few hours. The suspension was filtered and the solid washed with acetone and methyl-tert-butyl ether.

The solid was dried under vacuum for one night.

About 0.7 kg of melphalan hydrochloride were obtained.

The invention claimed is:

1. A process for the purification of melphalan comprising:

(a) treating a compound of formula IV

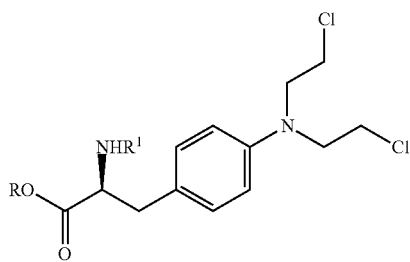

IV wherein R is hydrogen or a linear or branched $C_1$-$C_6$ alkyl group and $R_1$ is hydrogen or an amine protective group;

or a hydrochloric salt or a dimeric form thereof, in HCl 37% under reflux; and (b) isolating the compound obtained from step (a) in the presence of water, methyl-tert-butyl ether and diethylamine at pH=2.

2. A process according to claim 1 further comprising washing the compound obtained from step (b) with a linear or branched $C_1$-$C_4$ alcohol.

3. A process for the preparation of melphalan comprising:

(a) alkylating a compound of formula II

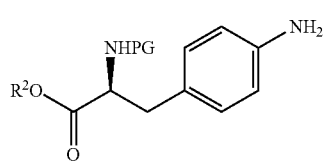

II wherein $R^2$ is a linear or branched $C_1$-$C_6$ alkyl group and PG is an amine protective group;

in the presence of an aprotic polar solvent, a base and an alkylating agent, to give a compound of formula III

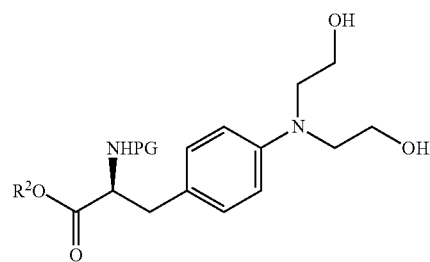

III (b) chlorinating the resultant compound of formula III in the presence of a chlorinating agent in a suitable solvent to give a compound of formula IV-1

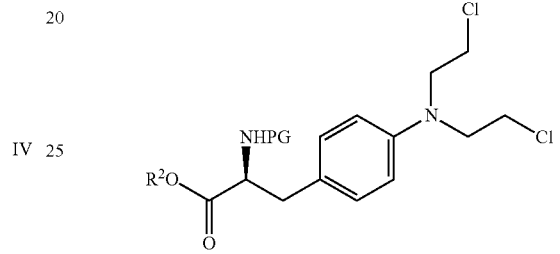

IV-1

(c) isolating and purifying of the melphalan comprising:
   (i) treating a compound of formula IV-1 in HCl 37% under reflux;
   (ii) isolating the compound obtained from step (i) in the presence of water, methyl-tert-butyl ether and diethylamine at pH=2;
   (iii) washing of the compound obtained from step (ii) with a linear or branched $C_1$-$C_4$ alcohol; and (d) optionally treating the compound obtained from step (iii) with a mineral acid.

4. A process according to claim 3 wherein in step (a) the aprotic polar solvent is selected from the group consisting of acetonitrile and dichloromethane and the base is selected from the group consisting of $Na_2CO_3$, $K_2CO_3$, $Cs_2CO_3$ and CaO.

5. A process according to claim 3 wherein in step (b) the chlorinating agent is $POCl_3$ or $SOCl_2$.

6. A process according to claim 1 wherein in step (a) HCl 37% is used in a ratio HCl 37%/melphalan of about 4:1.

7. A process according to claim 1 wherein in step (b) the ratio water/melphalan is of about 10:1.

8. A process according to claim 1 wherein in step (b) the ratio methyl-tert-butyl ether/water is of about 2:1.

9. A process according to claim 3 wherein in step (d) the mineral acid is an ethanol solution of gaseous HCl in acetone.

10. A process comprising:
    (a) alkylating the amine group on the aromatic ring of N-BOC-L-phenylalanine ethyl ester in the presence of acetonitrile, $Na_2CO_3$ and iodoethanol to give 4-(bis-(2 hydroxyethyl)-amino-N-BOC-L-phenylalanine ethyl ester;
    (b) chlorinating the compound obtained from step (a) in the presence of $POCl_3$ and isopropylacetate;
    (c) isolating and purifying of the melphalan comprising:
        (i) treating the compound obtained from step (b) in HCl 37% under reflux;

(ii) isolating the compound obtained from step (i) in the presence of water, methyl-tert-butyl ether and diethylamine at pH=2; and (iii) washing of the compound obtained from step (ii) with ethanol; and (d) converting the compound obtained from step (iii) into melphalan hydrochloride by treatment with an ethanol solution of gaseous HCl in acetone.

11. The process of claim 1, wherein the Melphalan and melphalan hydrochloride have an HPLC purity >99.5%.

12. The process of claim 11, wherein the impurity G level for the Melphalan or melphalan hydrochloride is NMT 0.5%.

* * * * *